United States Patent [19]
Lisi et al.

[11] Patent Number: 5,908,754
[45] Date of Patent: Jun. 1, 1999

[54] METHOD FOR IN VITRO DETERMINATION OF IN VIVO ERYTHROPOEITIN BIOACTIVITY

[75] Inventors: Peter J. Lisi, Flemington; Jeffrey K. Glenn, Middlesex; Chi-Kwong So, Somerville, all of N.J.

[73] Assignee: Ortho Pharmaceutical Corporation, Raritan, N.J.

[21] Appl. No.: 08/948,387

[22] Filed: Oct. 10, 1997

Related U.S. Application Data

[63] Continuation of application No. 08/772,955, Dec. 24, 1996, abandoned, which is a continuation of application No. 08/495,730, Jun. 8, 1995, abandoned, which is a continuation of application No. 08/107,390, Aug. 16, 1993, abandoned.

[51] Int. Cl.⁶ .............................. C12Q 1/68; C12Q 1/00; G01N 33/53
[52] U.S. Cl. ................................ 435/6; 435/4; 435/7.1
[58] Field of Search ...................... 435/4, 7.1, 6

[56] References Cited

PUBLICATIONS

Broudy et al. (1990) Blood, vol. 75(8): 1622–1626.
Lewis et al. (1989) Exp. Hematol. 17: 102–105.
Takeuchi et al. (1989) Proc. Natl. Acad. Sci., vol. 86: 7819–7822.
Viscata et al. (May 5, 1991) Cancer Research, vol. 51: 2515–2520.
Lodish, (1991) Trends in Biochem. Sci, vol. 16: 374–377.
Watson et al., LC–GC, vol. 11, (3) (1993), pp. 216, 218–220.
Paul et al, Exp. Hematol. (NY) 15(4), 1987, pp. 382–388.

*Primary Examiner*—Lisa B. Arthur
*Attorney, Agent, or Firm*—Alan J. Morrison

[57] ABSTRACT

The present invention is directed to an in vitro method of determining the in vivo EPO activity of a sample containing EPO. More particularly, the present method comprises treating a sample containing EPO under conditions which remove desialylated EPO, and measuring the in vitro EPO activity of the resulting treated sample. In a preferred embodiment, desialylated EPO is removed from the sample by incubating the sample with cells of the human hepatoma cell line HepG2, and in vitro EPO activity is determined by incubating the treated sample with cells of an EPO-responsive cell line and measuring the proliferation or viability of the EPO-responsive cells. The present invention is useful, for example, in quantitating the biologically active EPO in a variety of sample types.

12 Claims, No Drawings

METHOD FOR IN VITRO DETERMINATION OF IN VIVO ERYTHROPOEITIN BIOACTIVITY

This application is a continuation of application Ser. No. 08/772,995 filed Dec. 24, 1996, now abandoned, which is a continuation of application Ser. No. 08/495,730, filed Jun. 8, 1995, now abandoned; which is a continuation of Ser. No. 08/107,390, filed Aug. 16, 1993, now abandoned.

FIELD OF THE INVENTION

Erythropoietin (EPO) is a glycoprotein hormone which stimulates the maturation of erythroid precursor cells and thereby regulates the production of erythrocytes in mammals. The purification of human EPO (hEPO) and the cloning of the EPO gene have led to the commercial production of recombinant hEPO, which has been successfully used in the treatment of patients with anemia due to renal failure, and is clinically useful in the treatment of other anemias. Present methods of quantitating the biologically active EPO in a sample, for example a bulk drug formulation, are cumbersome, expensive and time-consuming. The present invention provides a safe, rapid and relatively inexpensive method of measuring the in vivo bioactivity of EPO, and kits for measuring EPO bioactivity.

BACKGROUND OF THE INVENTION

EPO is a glycoprotein hormone which stimulates the proliferation, differentiation and maturation of erythroid precursor cells to mature red blood cells. EPO has been purified (Miyake et al., (1977) *J. Biol. Chem.* 252: 5558) and molecularly cloned (Lin et al. (1985) *Proc. Natl. Acad. Sci. USA* 82: 7580), and recombinant hEPO has been used successfully in the treatment of anemia due to end stage renal disease. Clinical use of EPO has also been reported in the treatment of anemia associated with AIDS, rheumatoid arthritis, hematological malignancies, and prematurity, and to increase the yield of autologous blood collected preoperatively.

Recombinant hEPO has a molecular mass of 30.4 kD, of which 40% is carbohydrate. Studies of the nature and function of the glycosylation of EPO have determined that the majority of the oligosaccharide chains of hEPO are fucose-containing, sialylated tetraantennary oligosaccharides. The glycosylation structure of human urinary EPO and recombinant EPO produced in Chinese hamster ovary (CHO) cells, baby hamster kidney (BHK) cells and human B-lymphoblastic cells is similar but not identical.

Glycosylation appears to play a role in solubility, biosynthesis and secretion of EPO, and in vivo metabolism of EPO. The in vivo metabolic role of glycosylation, and in particular the presence of sialic acid, has been investigated. It has been demonstrated that urinary and recombinant desialylated EPO lose in vivo activity due to rapid hepatic clearance. From these and similar studies it has been determined that sialic acid caps the penultimate galactose residue and thus protects EPO from clearance by hepatic asialoglycoprotein (galactosyl) receptors. Accordingly, loss of terminal sialic acid residues from the oligosaccharides of EPO exposes the galactose residues, resulting in rapid clearance of desialylated (also referred to as asialylated) EPO from the plasma via binding to the hepatic receptor.

Although desialylated EPO is essentially biologically inactive in vivo due to its rapid clearance, its bioactivity is maintained in established in vitro assays. Standard assays for determining bioactivity of EPO in vitro include measurement of incorporation of tritiated thymidine by splenic erythroblasts from phenylhydrazine-treated anemic mice (Krystal (1983) *Exp. Hematol.* 20: 649) or cells of a human pluripotent leukemia cell line (Lewis et al. (1989) *Exp. Hematol.* 17: 102), measurement of incorporation of $^{59}Fe$ into cultured bone marrow cells (Goldwasser et al. (1975) *Endocrinology* 97: 315), and measurement of the growth of EPO-dependent cell lines (Kitamura et al. (1989) *Blood* 73: 375).

Because the in vitro assays cannot discriminate between sialylated and desialylated EPO, such assays are not useful in quantitating the population of EPO which would be expected to be active in vivo. For example, if an EPO-containing sample also contains a significant amount of desialylated EPO, the in vitro assays would provide an overestimate of the in vivo activity. Accordingly, in vivo assays are used to measure the in vivo activity of EPO. Specifically, EPO activity is measured by incorporation of $^{59}Fe$ into erythroblasts of polycythemic mice (Cotes et al. (1961) *Nature* 191: 1065) or starved rats (Goldwasser et al. (1975) *Methods Enzymol.* 37: 109).

In a currently used assay which is a modification of the procedure of Cotes et al., female mice are exposed to hypobaric pressure for fourteen days. Endogenous red cell formation is suppressed by the polycythemia produced through exposure to reduced pressure. As the polycythemic state persists after hypoxia, any new red blood cell formation is attributable to the administration of exogenous EPO. The test samples and EPO standards are then injected subcutaneously into the conditioned mice. Forty-eight hours after EPO injection, $^{59}Fe$ is administered. Blood samples are drawn after another forty-eight hours, and radioactivity is quantitated. The quantity of radioactivity is directly proportional to the injected dose of standard EPO; the in vivo activity of unknown samples is calculated from a standard curve.

The in vivo bioassay is widely recognized as the only true measure of in vivo biological activity, since it measures both the circulating life and proliferative activity of EPO. However, the in vivo assay suffers from significant disadvantages in that it is labor-intensive, expensive, time-consuming, and subject to animal-to-animal variation.

The present invention provides an in vitro method of quantitating the in vivo activity of EPO which overcomes the disadvantages of the prior art methods.

SUMMARY OF THE INVENTION

The present invention is directed to an in vitro method for determining the in vivo EPO activity of a sample containing EPO. More particularly, the present method comprises treating a sample containing EPO under conditions which remove desialylated EPO, and measuring in vitro the EPO activity of the resulting treated sample. In a preferred embodiment, desialylated EPO is removed from the sample by incubating the sample with cells of the human hepatoma cell line HepG2, and in vitro EPO activity is determined by incubating the treated sample with cells of an EPO-responsive cell line and measuring the proliferation or viability of the EPO-responsive cells.

Another aspect of the invention provides a kit which comprises a first container containing cells which express the asialoglycoprotein receptor, and a second container which contains EPO-responsive cells. In another embodiment, the kit further comprises a third container containing a viability indicating dye, such as 3-[4,5-dimethylthiazol-2-yl]-2,5-diphenyltetrazolium bromide (MTT).

DETAILED DESCRIPTION OF THE INVENTION

The present invention is directed to an in vitro method for determining the in vivo EPO activity of a sample containing EPO. More particularly, the present method comprises treating a sample containing EPO under conditions which remove desialylated EPO, and measuring in vitro the EPO activity of the resulting treated sample. The present invention is particularly useful in determining the in vivo activity of EPO formulations intended for clinical use.

In vitro EPO activity is defined as the ability to stimulate the proliferation or viability, in vitro, of cells which express a functional EPO-receptor, for example, erythroid precursor cells. As discussed hereinbelow, both sialylated and desialylated EPO are active in vitro. In vivo EPO activity is defined as the ability to stimulate the proliferation of erythroid precursor cells in vivo. Desialylated EPO is considered herein to be essentially inactive in vivo due to rapid hepatic clearance.

In accordance with the present invention, an EPO-containing sample can be particulate or liquid, and preferably is serum or plasma, cell culture media, purified or partially purified recombinant EPO, or an EPO formulation intended for clinical use, stability or formulation studies.

According to the present invention, the EPO-containing sample is treated under conditions which remove desialylated EPO. Desialylation of EPO results in the exposure of the penultimate galactose residues of the oligosaccharides of EPO. Accordingly, desialylated EPO can be removed from an EPO-containing sample by subjecting the sample to affinity chromatography with a lectin which has affinity for galactose, for example Abrin A or by affinity chromatography with an immobilized antibody specific for galactose. Methods for performing lectin affinity chromatography are known to the ordinarily skilled artisan.

In another embodiment, desialylated EPO is removed from an EPO-containing sample by incubation with cells which express the asialoglycoprotein receptor. The cells may naturally express the asialoglycoprotein receptor, or may be engineered to express the receptor recombinantly. For example, fibroblasts transfected with cDNA encoding the HL-1 and HL-2 subunits of the asialoglycoprotein receptor express a functional receptor. Transfected fibroblasts expressing the recombinant asialoglycoprotein receptor can be obtained by following the procedure of Shia et al. (1989) *Proc. Natl. Acad. Sci. USA* 86: 1158.

In a preferred embodiment, desialylated EPO is removed from an EPO-containing sample by incubation with cells of the human hepatoma cell line HepG2 (ATCC No. HB 8065), which are known to naturally express a functional asialoglycoprotein receptor at high density (see, for example, Lodish, (1991) *Trends in Biochem. Sciences* 16: 374). The HepG2 cell line is described by Knowles et al. (1980) *Science* 209: 497 and in U.S. Pat. No. 4,393,133 to Knowles et al.

Appropriate conditions for incubating the EPO-containing sample with cells which express the asialoglycoprotein receptor can be determined by the skilled artisan and may vary depending upon the cell type and source of the sample. In one embodiment, cells are grown to subconfluence, washed, and cell suspensions are added to wells of a tissue culture plate. Each well containing the adherent cells is washed several times with buffer, buffer is removed, and EPO standards or test samples are added to each well. The cells and EPO-containing samples are incubated overnight (about 15–20 hours) at 37° C. in a humidified atmosphere of 5% $CO_2$ and 95% air. The supernatants from the incubation mixtures, which are termed the "treated samples" in accordance with the present invention and from which desialylated EPO has been adsorbed, are subsequently transferred to vessels for analysis of EPO proliferative activity.

In order to confirm that desialylated EPO has been removed either by affinity chromatography or incubation with cells expressing the asialoglycoprotein receptor, EPO can be subjected to desialylating conditions. Chemical and enzymatic methods for desialylation are known to the ordinarily skilled artisan. Briefly, EPO can be chemically desialylated by heating at 80° C. for 60 minutes in 0.1 mol/L HCl. Desialylation can also be accomplished by incubating EPO with immobilized neuraminidase. Specific conditions for desialylation of EPO are described by Spivak et al. (1989) *Blood* 73: 90. An analysis of EPO before and after desialylation, for example by isoelectric focusing, can be used to determine whether sialic acid has been removed.

Following treatment of the EPO-containing sample to adsorb desialylated EPO as described above, the EPO proliferative activity of the treated sample is assessed. As described above, the term "treated sample" refers to a sample which has been treated to remove desialylated EPO, for example by lectin affinity chromatography or by incubation with cells which express a functional asialoglycoprotein receptor. The treated sample can be, for example, a cell culture supernatant.

The proliferative activity can be determined, for example, by measuring changes in cell number or DNA synthesis of EPO-responsive cells in response to incubation with the treated sample. In accordance with the present invention, EPO-responsive cells are defined as cells which proliferate or retain viability in response to EPO. EPO-responsive cells which can be used to measure the in vitro proliferative activity of EPO include erythroid progenitor cells freshly explanted from hematopoietic organs, established cell lines which naturally express EPO receptors, and established cell lines which have been engineered to express the EPO receptor gene. Cell lines which naturally express EPO receptors are generally derived from malignant cells of tumor-bearing animals. For example, murine erythroid cell lines have been established from erythroleukemic mice infected with the Friend leukemia virus complex or the Rauscher leukemia virus complex. Human cells lines have been established from leukemic patients. Other cell lines have been engineered to produce large numbers of EPO receptors and to require EPO for survival by introduction and expression of the EPO receptor gene. EPO-responsive cell systems are known to the ordinarily skilled artisan and have been reviewed by Koury et al. (1992) *Eur. J. Biochem.* 210: 649.

In a preferred embodiment, the EPO-responsive cells are cells of the multipotential hematopoietic progenitor cell line B6SUtA described by Greenberger et al. (1983) *Proc. Natl. Acad. Sci. USA* 80: 2931. The B6SUtA cell line was derived from long-term bone marrow cultures of B6.S mice.

Proliferation of EPO responsive cells can be measured by quantitating increased DNA synthesis in response to EPO. Increased DNA synthesis is typically determined in vitro by measuring tritiated thymidine incorporation. Appropriate assays are known in the art and described, for example, by Krystal et al. (1983) *Exp. Hematol.* 11: 649 and Lewis et al. (1989) *Exp. Hematol.* 17: 102. Briefly, preparations of EPO-responsive cells are incubated with EPO-containing test samples in microtiter plate wells, typically for 22 hours at 37° C. in a humidified atmosphere of 5% $CO_2$ and 95% air. Tritiated thymidine is added to a final concentration of about 0.1 $\mu$Ci/well. Following an additional two hour incubation, well contents are collected on glass fiber filters and the radioactivity recovered is measured by scintillation spectrometry. For standardization, the amount of radioactivity incorporated into DNA is plotted versus the EPO activity in mU/ml.

In a preferred embodiment which avoids the use of radioactivity, proliferation of EPO-responsive cells is measured spectrophotometrically through the use of the dye MTT (3-[4,5-dimethylthiazol-2-yl]-2,5-diphenyl tetrazolium bromide) (Mossman, 1983, *Immunological Methods*

65, 55). MTT is a yellowish color in solution, and is converted to dark blue/purple water-insoluble MTT formazin by mitochondrial dehydrogenases of living cells. The blue crystals are solubilized with acidic isopropanol and intensity is measured colorimetrically at 570 and 690 nm. Accordingly, the amount of MTT converted to the colored formazin is a direct measure of cell number which is an indicator of cell proliferation. A comparison of the optical densities of unknowns to standards is used to calculate biological activity. In a preferred embodiment, the treated sample is incubated with EPO-responsive cells in the wells of a microtiter plate for about 46–50 hours at 37° C. in a humidified atmosphere of 5% $CO_2$ and 95% air. MTT is then added to each well and incubated for two hours at 37° C. Following solubilization of the blue crystals, optical densities are measured and EPO activity is determined by comparing the cell numbers produced by an unknown sample to an EPO standard curve. MTT is commercially available, as are kits which contain MTT dye and solubilization solution (MTT Kit, Promega Corporation). In addition to MTT, other indicator dyes such as XTT (3,3'-(1-((phenylamino) carbonyl)-3,4-tetrazolium)-bis(4-methoxy-6-nitro) benzenesulfonic acid, sodium salt) and MTS (3-(4,5-dimethylthiazol-2-yl)-5-(3-carboxymethoxyphenyl)-2-(4-sulfophenyl)-2H-tetrazolium, inner salt) may be used for the same purpose.

In a preferred embodiment of the method of the present invention, desialylated EPO is removed from the sample by incubating the sample with cells of the human hepatoma cell line HepG2, and in vitro EPO activity is determined by incubating the treated sample, i.e. the supernatant from the HepG2 cells, with cells of an EPO-dependent cell line, and measuring the proliferation or viability of the EPO-dependent cells. In a most preferred embodiment which is exemplified hereinbelow at Example 1, the EPO-dependent cell line is B6SUtA and cell proliferation or viability is measured spectrophotometrically through the use of MTT.

It has been found in accordance with the present invention that the in vitro affinity of the asialoglycoprotein receptor of HepG2 cells for desialylated EPO effectively mimics the in vivo function of rapid clearance of desialylated EPO. Further, it has been found that cell culture media which contains EPO can induce proliferation of EPO-responsive cells.

Another aspect of the present invention provides a kit for determining the in vivo EPO activity of a sample containing EPO. In one embodiment, the kit is compartmentalized to receive a first container containing cells which express the asialoglycoprotein receptor, and a second container which contains EPO-dependent cells. In a preferred embodiment, the cells which express the asialoglycoprotein receptor are HepG2 cells and the EPO-dependent cells are B6SUtA cells. In another embodiment, the kit further comprises a third container which contains MTT.

The following example further illustrates the present invention. The invention is not to be considered limited by these examples, but only by the appended claims.

EXAMPLE 1

HepG2 cells are grown in 100 mm tissue culture plates until confluence is reached. At this point the cells are washed with phosphate buffered saline, trypsinized to detach them from the plate and a $0.25 \times 10^6$ cells/ml suspension in cell culture medium is made. One ml of this suspension is added to each well of a 24-well tissue culture plate. Three days later the HepG2 cells are ready to be used in an EPO assay.

Each well containing HepG2 cells is washed five times with phosphate buffered saline (PBS). After the PBS is entirely removed, 100 μl of medium (Dulbecco's MEM containing 10% fetal calf serum and glutamine) is added to each well. An EPO standard curve is initiated by taking an EPO reference standard at 10 U/ml and diluting this two-fold by mixing 100 μl of each solution added to a separate well. The cells plus EPO solutions are incubated overnight at 37° C. in a 5% $CO_2$ high humidity incubator. After incubation, the standard curve is prepared by diluting the HepG2-treated 5 U/ml standard five-fold in medium to give a 1 U/ml solution. Each treated sample is diluted 10-fold in medium to give estimated 0.5 U/ml solutions. The standards and samples are then ready for the proliferation assay. At about the same time that the standard and samples are added to the HepG2 cells, B6SUtA cells are prepared for the proliferation assay to be started the next day. These cells have been growing in medium (as described above) and supplemented with 20 ng/ml IL-3; passaged twice per week at a 1:20 dilution. The cells are prepared by washing once with medium and reconstituted to the original volume in medium without IL-3. The cells are incubated overnight in 100 mm plates (37° C., 5% $CO_2$). After incubation, the cells are washed again in medium and resuspended at a final concentration of $1 \times 10^6$ cells/ml. Using a 96-well tissue culture plate, 50 μl of B6SUtA cells are mixed with 50 μl of each EPO standard and sample. The plate is incubated 48 hours at 37° C. in a 5% $CO_2$ incubator.

Cell proliferation or viability is measured with the MTT Kit from Promega Corp. The amount of MTT converted to a colored formazin is directly related to the number of cells. The procedure, in brief is as follows. Twenty μl of MTT dye (Promega Corp.) is added to each well and incubated for 2 hours at 37° C. Then 100 μl of the Solubilization Solution (Promega Corp.) is added to each well and incubated at room temperature until all the dark blue/purple precipitate dissolves, usually 1–4 hours. The plate is then read in a plate reader at O.D. 570 nm and 690 nm. EPO activity is determined by comparing the number of cells produced by an unknown sample to the EPO standard curve. Potency is calculated by dividing calculated activity by 0.5 U/ml and multiplying by 100%.

Table 1 presents representative optical densities and calculated values of EPO standards ranging in concentration from 0–1000 mU/ml determined under the above conditions. As can be seen from the calculated values, the method of the present invention provides an accurate measurement of the EPO standards.

When the same standards are assayed for proliferative activity in the absence of pre-incubation with HepG2 cells, similar results are obtained, as presented in Table 2. These results indicate that the HepG2 cell treatment does not significantly affect the EPO standard curve.

Samples with known and varying amounts of desialylated EPO were assayed by the present method and also in the absence of pre-incubation with HepG2 cells. As can be seen from Table 3, samples containing significant amounts of desialylated EPO induce a greater proliferative response before incubation with HepG2 cells (R2) than after incubation with HepG2 cells and adsorption of desialylated EPO (R1). Table 3 also provides the expected quantities of sialylated (intact) EPO and the values calculated from the optical densities obtained in accordance with the present method. As can be seen from Table 3, the present method is highly accurate in quantitating the amount of sialylated (i.e. in vivo active) EPO in a sample.

The present invention has been described herein with reference to certain preferred embodiments and an example. Since obvious variations will appear to those skilled in the art, the invention is not to be considered limited thereto, but only by the claims which follow.

TABLE 1

EPO Activity of Standards
Following Pre-Incubation with HEPG2 Cells

| STANDARD | Std. Value | OD | Mean | Std Dev | CV | Calc. Value |
|---|---|---|---|---|---|---|
| STD00 | 1000 mU/ml. | 1.304 | 1.336 | 0.029 | 2.151 | 942.9 |
|  |  | 1.359 |  |  |  | 1080 |
|  |  | 1.346 |  |  |  | 1044 |
| STD01 | 900.0 mU/ml. | 1.244 | 1.271 | 0.057 | 4.494 | 824.6 |
|  |  | 1.233 |  |  |  | 805.6 |
|  |  | 1.337 |  |  |  | 1021 |
| STD02 | 800.0 mU/ml. | 1.223 | 1.240 | 0.037 | 2.951 | 788.9 |
|  |  | 1.215 |  |  |  | 775.9 |
|  |  | 1.282 |  |  |  | 896.4 |
| STD03 | 700.0 mU/ml. | 1.133 | 1.161 | 0.040 | 3.410 | 659.9 |
|  |  | 1.143 |  |  |  | 672.6 |
|  |  | 1.206 |  |  |  | 761.7 |
| STD04 | 600.0 mU/ml. | 1.114 | 1.109 | 0.019 | 1.713 | 636.6 |
|  |  | 1.088 |  |  |  | 606.6 |
|  |  | 1.125 |  |  |  | 649.9 |
| STD05 | 500.0 mU/ml. | 0.961 | 0.965 | 0.034 | 3.488 | 483.5 |
|  |  | 0.933 |  |  |  | 460.5 |
|  |  | 1.000 |  |  |  | 517.8 |
| STD06 | 400.0 mU/ml. | 0.827 | 0.846 | 0.025 | 2.950 | 383.0 |
|  |  | 0.874 |  |  |  | 415.6 |
|  |  | 0.836 |  |  |  | 389.0 |
| STD07 | 300.0 mU/ml. | 0.691 | 0.689 | 0.017 | 2.414 | 300.1 |
|  |  | 0.704 |  |  |  | 307.4 |
|  |  | 0.671 |  |  |  | 289.0 |
| STD08 | 200.0 mU/ml. | 0.477 | 0.496 | 0.016 | 3.261 | 192.6 |
|  |  | 0.505 |  |  |  | 205.6 |
|  |  | 0.505 |  |  |  | 205.6 |
| STD09 | 100.0 mU/ml. | 0.269 | 0.270 | 0.002 | 0.565 | 99.79 |
|  |  | 0.270 |  |  |  | 100.2 |
|  |  | 0.272 |  |  |  | 101.1 |
| STD10 | 0.000 mU/ml. | 0.093 | 0.096 | 0.006 | 6.720 | <<<<< |
|  |  | 0.091 |  |  |  | <<<<< |
|  |  | 0.103 |  |  |  | 10.30 |

TABLE 2

EPO Activity of Standards without
Pre-Incubation with HepG2 Cells

| STANDARD | Std. Value | OD | Mean | Std Dev | CV | Calc. Value |
|---|---|---|---|---|---|---|
| STD00 | 1000 mU/ml. | 1.439 | 1.517 | 0.069 | 4.566 | 923.1 |
|  |  | 1.539 |  |  |  | 1141 |
|  |  | 1.572 |  |  |  | 1236 |
| STD01 | 900.0 mU/ml. | 1.362 | 1.425 | 0.074 | 5.227 | 800.7 |
|  |  | 1.405 |  |  |  | 865.4 |
|  |  | 1.507 |  |  |  | 1062 |
| STD02 | 800.0 mU/ml. | 1.264 | 1.364 | 0.097 | 7.122 | 679.2 |
|  |  | 1.371 |  |  |  | 813.5 |
|  |  | 1.458 |  |  |  | 958.4 |
| STD03 | 700.0 mU/ml. | 1.251 | 1.278 | 0.054 | 4.240 | 665.2 |
|  |  | 1.242 |  |  |  | 655.7 |
|  |  | 1.340 |  |  |  | 770.6 |
| STD04 | 600.0 mU/ml. | 1.177 | 1.185 | 0.007 | 0.599 | 592.8 |
|  |  | 1.186 |  |  |  | 601.0 |
|  |  | 1.191 |  |  |  | 605.6 |
| STD05 | 500.0 mU/ml. | 1.071 | 1.083 | 0.011 | 1.028 | 505.9 |
|  |  | 1.085 |  |  |  | 516.4 |
|  |  | 1.093 |  |  |  | 522.6 |
| STD06 | 400.0 mU/ml. | 0.917 | 0.902 | 0.019 | 2.061 | 403.7 |
|  |  | 0.907 |  |  |  | 397.8 |
|  |  | 0.881 |  |  |  | 382.8 |
| STD07 | 300.0 mU/ml. | 0.724 | 0.744 | 0.035 | 4.732 | 300.8 |
|  |  | 0.785 |  |  |  | 331.1 |
|  |  | 0.724 |  |  |  | 300.8 |
| STD08 | 200.0 mU/ml. | 0.435 | 0.455 | 0.017 | 3.813 | 173.6 |
|  |  | 0.464 |  |  |  | 185.7 |
|  |  | 0.466 |  |  |  | 186.5 |
| STD09 | 100.0 mU/ml. | 0.271 | 0.281 | 0.009 | 3.225 | 104.6 |
|  |  | 0.288 |  |  |  | 112.0 |
|  |  | 0.285 |  |  |  | 110.7 |
| STD10 | 0.000 mU/ml. | 0.096 | 0.097 | 0.003 | 2.728 | <<<<< |
|  |  | 0.095 |  |  |  | <<<<< |
|  |  | 0.100 |  |  |  | 4.484 |

TABLE 3

Quantitation of Intact (Sialylated) EPO

| % Asialo EPO | R1 w/HepG-2. mU/ml | R2 w/o/HepG-2 mU/ml. | R2/R1 Ratio | k = 0.15 Calculated Intact EPO. mU/ml. | k = 0.15 Calculated % Intact EPO. | Expected Intact EPO. mU/ml. | Percent Accuracy |
|---|---|---|---|---|---|---|---|
| 0.00 | 289.10 | 303.60 | 1.05 | 286.54 | 1.00 | 300.00 | 0.96 |
| 10.00 | 268.60 | 352.80 | 1.31 | 253.74 | 0.89 | 270.00 | 0.94 |
| 20.00 | 261.70 | 424.20 | 1.62 | 233.02 | 0.81 | 240.00 | 0.97 |
| 30.00 | 254.70 | 494.20 | 1.94 | 212.44 | 0.74 | 210.00 | 1.01 |
| 40.00 | 217.60 | 555.40 | 2.55 | 157.99 | 0.55 | 180.00 | 0.88 |
| 50.00 | 214.60 | 628.30 | 2.93 | 141.59 | 0.49 | 150.00 | 0.94 |
| 60.00 | 213.40 | 693.60 | 3.25 | 128.66 | 0.45 | 120.00 | 1.07 |
| 70.00 | 192.30 | 755.50 | 3.93 | 92.91 | 0.32 | 90.00 | 1.03 |
| 80.00 | 196.10 | 959.90 | 4.89 | 61.31 | 0.21 | 60.00 | 1.02 |
| 90.00 | 178.60 | 999.20 | 5.59 | 33.79 | 0.12 | 30.00 | 1.13 |
| 100.00 | 150.80 | 1029.00 | 6.82 | −4.18 | −0.01 | 0.00 | #DIV/0! |

What is claimed is:

1. A method for the in vitro determination of the in vivo erythropoeitin (EPO) activity of an EPO-containing sample, which comprises (a) treating a portion of the sample under in vitro conditions by incubating with cells expressing surface asialoglycoprotein receptors so as to remove the desialylated EPO therein, thereby forming a treated and an untreated portion of the EPO sample, (b) measuring the in vitro EPO activity of the treated portion by incubating said treated portion with EPO-responsive cells and measuring proliferation or viability of said EPO-responsive cells, and (c) determining the ratio of in vitro activity of the untreated portion of the EPO sample to that of the treated portion, so as to determine the in vivo EPO activity of the EPO-containing sample.

2. The method of claim 1, wherein said cells are HepG2 cells.

3. The method of claim 1, wherein said EPO-responsive cells are B6SUtA cells.

4. The method of claim 1, wherein said proliferation of said EPO-responsive cells is measured by determining an increase in DNA synthesis.

5. The method of claim 4, wherein said increase in DNA synthesis is measured by determining tritiated thymidine incorporation.

6. The method of claim 1, wherein said proliferation of said EPO-responsive cells is measured spectrophotometrically.

7. The method of claim 1, wherein said proliferation of said EPO-responsive cells is measured by incubating said cells with 3-[4,5-dimethylthiazol-2-yl]-2,5-diphenyltetrazolium bromide (MTT) and measuring the conversion of MTT to MTT formazin.

8. A method for the in vitro determination of the in vivo erythropoeitin (EPO) activity of an EPO-containing sample, which comprises: (a) treating a portion of the sample by incubation with HepG2 cells so as to remove the desialylated EPO therein, thereby forming a treated and an untreated portion of the EPO sample; (b) removing supernatant resulting from said HepG2 cell incubation; (c) incubating said supernatant with B6SUtA cells; (d) measuring proliferation of said B6SUtA cells; (e) calculating the in vitro EPO activity based on said measurement; and (f) determining the ratio of in vitro activity of the untreated portion of the EPO sample to that of the treated portion, so as to determine the in vivo EPO activity of the EPO-containing sample.

9. The method of claim 8, wherein said sample containing EPO is incubated with said HepG2 cells for about 15 to 20 hours at 37° C. in a humidified atmosphere of 5% $CO_2$ and 95% air.

10. The method of claim 8, wherein said supernatant is incubated with said B6SUtA cells for about 46 to 50 hours at 37° C.

11. The method of claim 8, wherein said proliferation of said B6SUtA cells is measured by incubating said cells with MTT and measuring the conversion of MTT to MTT formazin.

12. The method of claim 8, wherein said in vitro EPO activity is calculated by comparing the proliferation produced by the EPO-containing sample to the proliferation produced by an EPO standard.

* * * * *